United States Patent [19]

Huang et al.

[11] 3,988,383
[45] Oct. 26, 1976

[54] INERT REMOVAL FROM CHLORINATED HYDROCARBON PRODUCTION SYSTEM

[75] Inventors: Chiung-Yuan Huang, Glen Ridge; Stephen J. Sopko, Clark, both of N.J.

[73] Assignee: The Lummus Company, Bloomfield, N.J.

[22] Filed: Jan. 31, 1975

[21] Appl. No.: 545,794

[52] U.S. Cl. .................... 260/652 P; 260/654 A; 260/654 S; 260/656 R; 260/659 A; 260/662 A
[51] Int. Cl.² ........................................ C07C 19/00
[58] Field of Search ........ 260/659 A, 662 A, 659 R, 260/652 P, 666 SA, 654 S, 654 A; 55/68, 71, 85

[56] References Cited
UNITED STATES PATENTS

| | | | |
|---|---|---|---|
| 2,402,978 | 7/1946 | Allen et al. | 55/71 |
| 2,498,552 | 2/1950 | Kilgren et al. | 260/659 A |
| 2,540,905 | 2/1951 | Neubauer et al. | 55/71 |
| 2,841,243 | 7/1958 | Hooker et al. | 260/652 P |
| 3,148,041 | 9/1964 | Dehn et al. | 260/659 A |

*Primary Examiner*—Delbert E. Gantz
*Assistant Examiner*—Joseph A. Boska
*Attorney, Agent, or Firm*—Marn & Jangarathis

[57] ABSTRACT

In the production of chlorinated hydrocarbons, a gas stream containing unreacted hydrocarbon, chlorinated hydrocarbon, carbon dioxide and inerts, such as, carbon monoxide and/or nitrogen, is contacted with a chlorinated hydrocarbon absorption oil to separate hydrocarbon, chlorinated hydrocarbon and carbon dioxide from inerts. The rich absorption solution is introduced into a stripper wherein chlorinated hydrocarbons are recovered as a sidestream, absorption solution as a bottoms and a hydrocarbon-carbon dioxide stream, containing a reduced amount of chlorinated hydrocarbons, as overhead. The overhead is introduced into a further absorption column, primarily designed to recover chlorinated hydrocarbons in the absorption solution, with a hydrocarbon overhead being withdrawn therefrom which is rich in carbon dioxide and is essentially free of low boiling chlorinated hydrocarbon, to thereby facilitate subsequent separation of carbon dioxide. The process is particularly applicable to the production of chlorinated methanes or vinyl chloride.

13 Claims, 1 Drawing Figure

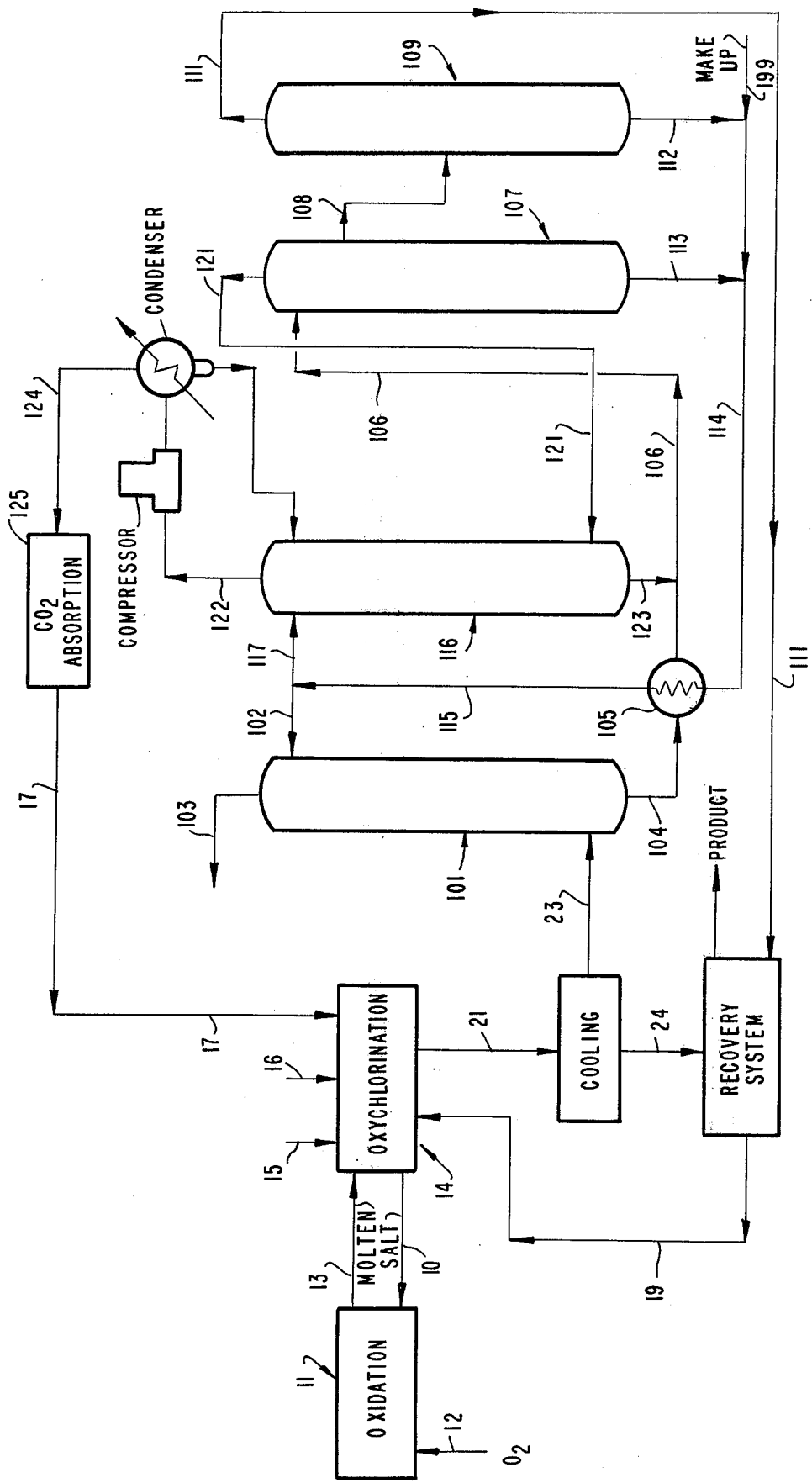

INERT REMOVAL FROM CHLORINATED HYDROCARBON PRODUCTION SYSTEM

This invention relates to the production of chlorinated hydrocarbons, and more particularly, to a new and improved process for removing inerts from an effluent withdrawn from a chlorinated hydrocarbon production zone.

In the production of chlorinated hydrocarbons, inerts, such as nitrogen and/or carbon monoxide, are generally present in the chlorinated hydrocarbon effluent. Accordingly, in order to prevent a build-up of such inerts in the system, there is a necessity to purge such inerts from the system.

An object of the present invention is to provide an improved process for producing chlorinated hydrocarbons.

Another object of the present invention is to provide for removal of inerts from a system for producing chlorinated hydrocarbons.

A further object of the present invention is to provide for removal of inerts, while simultaneously conditioning the system for removal of carbon dioxide.

These and other objects of the present invention should be more readily apparent from reading the following description thereof.

In accordance with the present invention, there is provided a process for producing chlorinated hydrocarbon wherein a gaseous stream, containing unreacted hydrocarbon, chlorinated hydrocarbon, carbon dioxide, and as inerts, carbon monoxide and/or nitrogen, is contacted when a liquid absorbent to absorb hydrocarbon, chlorinated hydrocarbon(s) and carbon dioxide from the gaseous stream. The liquid absorbent is separated from the gaseous stream, and introduced into a stripper operated at temperatures and pressures to recover absorbed chlorinated hydrocarbons as a sidestream, hydrocarbon and carbon dioxide as overhead and lean absorption solution, as bottoms. The overhead from the stripper, which includes some quantities of chlorinated hydrocarbon, is then introduced into a further absorption zone wherein the gaseous overhead is contacted with a chlorinated hydrocarbon absorption liquid in order to absorb remaining low boiling chlorinated hydrocarbons therefrom. The hydrocarbon gas stream withdrawn from the second absorber is rich in carbon dioxide and essentially free of at least the low boiling chlorinated hydrocarbons(s): i.e. chlorinated hydrocarbons boiling below chloroform (B.P. 142° F.). This gaseous stream may then be introduced into a carbon dioxide absorption zone in order to separate carbon dioxide therefrom. It has been found that by conditioning the hydrocarbon stream containing carbon dioxide, to essentially eliminate therefrom at least the low boiling chlorinated hydrocarbon(s); i.e. chlorinated hydrocarbons boiling below 140° F., the useful life and operation of the carbon dioxide absorption system is improved. As should be apparent, the chlorinated hydrocarbon absorption liquid should have a boiling point of at least 140° F.

The chlorinated hydrocarbon effluent treated in accordance with the present invention may be produced by any one of a wide variety of oxychlorination processes known in the art, which, as known in the art, are effected in the presence of a Deacon or oxychlorination type of catalyst. The general processes for producing chlorinated hydrocarbons by oxychlorination are well known in the art and no detailed description thereof is deemed necessary for a complete understanding of the present invention.

Although the process of the present invention is generally applicable to the oxychlorination of hydrocarbons, the process is particularly suitable for the oxychlorination of $C_1$–$C_4$ aliphatic hydrocarbons (both saturated and olefinically unsaturated), and in particular, to the oxychlorination of methane to produce chlorinated methane(s); and ethane and/or ethylene to produce chlorinated $C_2$ hydrocarbons. In accordance with such a process, a molten mixture, containing cuprous chloride, cupric chloride and a suitable melting point depressant; in particular, potassium chloride, is contacted with molecular oxygen, in a first reaction (oxidation) zone, to produce copper oxychloride. A molten mixture, containing cuprous chloride, cupric chloride and copper oxychloride, withdrawn from the first reaction zone is contacted in a second reaction (oxychlorination and chlorination) zone with hydrocarbon and hydrogen chloride and/or chlorine to produce chlorinated hydrocarbon. The feed to the second reaction zone, as required, generally also includes chlorinated hydrocarbon as recycle. Molten salt from the second reaction zone is then recycled to the first reaction zone.

In general, the second reaction zone is operated at a temperature from 700° to 1200° F, preferably 700° F to 950° F, with higher selectivity being obtained at temperatures from 700° to 860° F, preferably 800° to 850° F. The operating pressures are generally in the order of 1 to 10 atm.

The first reaction (oxidation) zone is generally operated at temperatures from 700° to 950° F, and preferably from 800° and 900° F, with the operating pressure generally being in the order of 1 to 10 atm.

The chlorinated hydrocarbons which are recycled to the oxychlorination reaction zone are determined by the desired reaction product. As should be apparent, if all chlorinated hydrocarbons are desired as product in the proportions produced there need be no recycle of chlorinated hydrocarbon. In the production, for example, of vinyl chloride by the use of ethane and/or ethylene, 1,2-dichloroethane produced in the oxychlorination is recovered and dehydrochlorinated in a separate reaction zone.

Particular processes for producing chlorinated methanes by the use of molten salts are described in U.S. Pat. application Ser. No. 299,848, filed Oct. 24, 1972, and U.S. Pat. application Ser. No. 299,114, filed on Oct. 19, 1972, both of which are hereby incorporated by reference.

Particular processes for chlorination (oxychlorination) of ethane and/or ethylene by the use of molten salts are described in U.S. Pat. application Ser. No. 153,374, filed on June 15, 1971 and U.S. Pat. application Ser. No. 157,496, filed on June 28, 1971, all incorporated by reference.

The gaseous stream, containing unreacted hydrocarbon, inerts,, carbon dioxide, chlorinated hydrocarbons, employed as feed to the inert purging system may be separated from the chlorinated hydrocarbon effluent by any one of a wide variety of procedures. In general, the chlorinated hydrocarbon effluent also includes water vapor and a convenient method of separating the water vapor from the effluent gas is by cooling to condense water vapor therefrom, with such cooling also generally resulting in the condensation of some chlorinated hydrocarbon components from the gaseous effluent, whereby a gaseous stream containing unreacted hydrocarbon, inerts, carbon dioxide and remaining chlorinated hydrocarbons is recovered from the cooling operation. In general, such a gaseous stream can be recovered by cooling the chlorinated hydrocarbon effluent in one or more cooling stages (which can be indirect cooling stages or direct quench cooling) to a temperature from about 40° F. to about 150° F, at pressures from about 100 psig to about 200 psig.

Although the above operation is preferred, it is to be understood that the gaseous stream containing hydrocarbon, carbon dioxide, inerts and chlorinated hydrocarbons can be recovered by other means; e.g., fractionation.

The invention will be further described with respect to an embodiment illustrated in the accompanying drawing wherein:

The DRAWING is a simplified schematic flow diagram of an embodiment of the invention.

Referring now to the drawing, a molten salt mixture including cuprous chloride, cupric chloride and a melting point depressant, in particular potassium chloride, in line 10, is introduced into an oxidation reaction zone 11 wherein the molten salt is contacted with molecular oxygen, introduced through line 12, to produce copper oxychloride.

A molten salt mixture, containing cuprous chloride, cupric chloride and copper oxychloride withdrawn from oxidation zone 11, through line 13 is introduced into a methane oxychlorination reaction zone 14 wherein the molten salt is contacted with fresh feed methane, introduced through line 15, hydrogen chloride, chlorine or mixtures thereof, introduced through line 16, a recycle methane stream, introduced through line 17, obtained as hereinafter described, and a recycle chlorinated methane stream, introduced through line 19. As hereinabove described, as a result of such contact, methane is oxychlorinated to chlorinated methanes.

Molten salt recovered from reaction zone 14 is recycled to oxidation reaction zone 11 through line 10.

A chlorinated methane effluent, containing chlorinated methanes, unreacted methane, water vapor, carbon dioxide, oxygen, and as inerts, nitrogen and carbon monoxide, is withdrawn from reaction zone 14 through line 21 and introduced into a cooling system, schematically indicated as 22. In the cooling system 22, the effluent is cooled in one or more stages to condense water vapor therefrom. In effecting such water condensation, a major portion of the heavier chlorinated methanes are condensed from the effluent and there is recovered a gaseous stream comprised of methane and lighter components (carbon monoxide, carbon dioxide and nitrogen), as well as chlorinated methanes, which is withdrawn from zone 22 through line 23.

The remainder of the chlorinated hydrocarbon effluent is withdrawn from zone 22 through line 24 and is introduced into a recovery system to recover desired chlorinated methane product, and chlorinated methanes for recycle to the methane oxychlorination reaction zone through line 19.

The gaseous stream in line 23, containing methane, carbon dioxide, inerts and chlorinated methanes, is introduced into an absorption column 101 wherein the gaseous stream is countercurrently contacted with a non-lower boiling (boiling point of at least 140° F.) chlorinated hydrocarbon absorption liquid, which is either carbon tetrachloride, chloroform, or a mixture thereof, preferably carbon tetrachloride, introduced through line 102. The absorption column is generally operated at a temperature from about 0° F. to about 170° F. and at a pressure from about 100 psig to about 300 psig. As a result of the countercurrent contact in absorption column 101 methane, carbon dioxide and chlorinated methanes are absorbed from the gaseous stream.

A gaseous stream, comprised of the inerts, is withdrawn from column 101 through line 103 for purging from the system. The gas in line 103 may contain some quantities of methane as well as some vaporized absorption oil, and the heating value of such methane may be recovered, prior to purging the gas from the system.

A rich absorption solution containing the bulk of the gas stream introduced into column 101; in particular, methane, chlorinated methanes, carbon dioxide, as well as some of the inerts, is withdrawn from column 101 through line 104, passed through heat exchanger 105 wherein the rich absorption solution is heated by indirect heat transfer with lean absorption solution, and introduced through line 106 into a stripping column 107, designed and operated to strip absorbed components from the absorption solution. In particular, the stripping column 107 is designed and operated to recover lean absorption solution as bottoms, chlorinated methane(s) as a sidestream, and lighter components as overhead. In general, the stripping column is operated at an overhead temperature from about 40° to about 150° F, a bottoms temperature from about 200° to about 300° F. and a column pressure from about 10 psig to about 90 psig. The stripping column may be provided with suitable reboil (not shown).

A sidestream comprised of the bulk of the chlorinated methane introduced as absorbed components in the absorption solution; i.e., including some carbon tetrachloride, is withdrawn from column 107 through line 108 and introduced into a stripping or fractional distillation column 109, designed and operated to recover carbon tetrachloride, as bottoms, and carbon tetrachloride in combination with lighter chlorinated hydrocarbon components as overhead. In general, the column 109 is operated at an overhead temperature from about 200° to about 300° F. and a column pressure from about 10 psig to about 100 psig. An overhead, comprised of carbon tetrachloride and lighter chlorinated hydrocarbons is withdrawn from column 109 through line 111 for introduction into the chlorinated hydrocarbon recovery system. A bottoms comprised of carbon tetrachloride is withdrawn from column 109 through line 112 for recycle to the absorption columns of the inert purging system. It is to be understood that column 109 primarily functions to insure that there is an adequate supply of absorption solution for the purging system; i.e., to recover any absorption oil present in the sidestream. If the sidestream withdrawn from column 107 contains only net carbon tetrachloride introduced into the purging system, column 109 could be eliminated.

A bottoms, comprised of carbon tetrachloride, is withdrawn from stripping column 107 through line 113, combined with carbon tetrachloride bottoms in line 112, and make-up introduced through line 199, and the combined stream, in line 114, passed through heat exchanger 104 wherein the carbon tetrachloride is cooled by indirect heat transfer with the lean absorption solution. The carbon tetrachloride in line 115 is then employed as an absorption oil for column 101, through line 102, and as an absorption oil in column 116, through line 117, as hereinafter described.

The overhead withdrawn from column 107 through line 121, comprised of methane, carbon dioxide, some inerts and some chlorinated hydrocarbon, is introduced into the absorption column 116 wherein the gas is countercurrently contacted with the carbon tetrachloride absorption oil introduced through line 117. In general, column 116 is operated at a temperature from about 0° F. to about 170° F. and a pressure from about 100 psig to about 300 psig. The carbon tetrachloride lean oil is provided at a rate to selectively absorb chlorinated hydrocarbon.

As a result of the countercurrent contact in column 116, the remaining portion of the lower boiling chlorinated hydrocarbons present in the gas stream are absorbed by the absorption oil, to produce a carbon dioxide rich overhead in line 122, which is compressed and condensed to recover carbon tetrachloride. The condensed portion is recycled to column 116. The carbon dioxide rich overhead in line 124 is essentially free of low boiling chlorinated hydrocarbon. It is to be understood that, in general, the overhead in line 124 contains no more than 1000 parts per million of low boiling chlorinated hydrocarbon, and preferably no more than 300 parts per million of low boiling chlorinated hydrocarbon.

The rich absorption solution is withdrawn from column 116 through line 123 and combined with the rich absorption solution in line 106 for introduction into the stripping column 107. In this manner, essentially all of the low boiling hydrocarbon(s) introduced through line 23 is eventually recovered in the sidestream 108 withdrawn from stripper 107.

The overhead in line 122 which is essentially free of low boiling hydrocarbon, and contains carbon dioxide and methane, as well as some inerts and vaporized carbon tetrachloride, is introduced into a carbon dioxide absorption system schematically designated as 125 wherein carbon dioxide is absorbed from the overhead.

The carbon dioxide is absorbed in zone 125 by the use of an acid gas absorption solution of a type known in the art. As representative examples of such acid gas absorption solutions, there may be mentioned; dioxolanes, sulfolanes, the various amines and alkanol amines, the carbonates and inorganic carbonates, such as sodium and potassium carbonate, etc. It has been found that the operation of the basic acid gas absorption system is improved as a result of the stream which is introduced into the system, being essentially free of lower boiling chlorinated hydrocarbons; i.e., the useful life of the system is increased.

As known in the art, the absorption zone 125 is preferably comprised of an absorption column wherein carbon dioxide is absorbed by lean absorption solution, and a stripper column wherein carbon dioxide is stripped from the rich absorption solution to produce lean absorption solution for use in the absorber.

A gas stream, essentially free of carbon dioxide, is withdrawn from the carbon dioxide absorption zone 125 (in particular as overhead from the absorption column) and recycled to reactor 14 through line 17. The gas stream is essentially comprised of methane.

Although the process has been particularly described with respect to a process for producing chlorinated methanes, the process is also applicable to the production of other chlorinated hydrocarbons. Thus, for example, the process could be employed for the oxychlorination of ethane and/or ethylene, in which case, a $C_2$ chlorinated hydrocarbon, (boiling point at least 140° F.) would be employed as an absorption oil; e.g., one or more of dichloroethane, trichloroethylene, tetrachloroethylene or heavier chlorinated $C_2$ hydrocarbons. Accordingly, the chlorinated hydrocarbon absorption oil has a number of carbon atoms corresponding to the carbon atoms of the hydrocarbon which is oxychlorinated.

Similarly, the feed to the inert purging system may be recovered from the chlorinated hydrocarbon effluent other than by a cooling process.

Furthermore, the feed to the purging system may include only lighter chlorinated methanes; e.g., methyl chloride and methylene chloride.

These and other modifications should be apparent to those skilled in the art from the teachings herein.

The invention will be further described with respect to the following example, but the scope of the invention is not to be limited thereby.

EXAMPLE

The following is illustrative of the invention for removal of low boiling chlorinated methanes:

Absorption Column 101 is operated at about 115° F. and 175 psig.

Absorption Column 116 is operated at about 155° F. and 35 psig.

Stripper 107 is operated at about 35 psig, an overhead temperature of about 180° F. and bottoms temperature of about 260° F.

Column 109 is operated at about 35 psig, an overhead temperature of about 160° F. and a bottoms temperature of about 245° F.

| | THE LUMMUS CO. MATERIAL BALANCE LB MOL/HR STREAM | | | | | | | |
|---|---|---|---|---|---|---|---|---|
| COMPONENT | 23 | 102 | 103 | 104 | 106 | 108 | 111 | 112 |
| $N_2$ | 6.39 | — | 3.76 | 2.63 | 2.69 | — | — | — |
| $O_2$ | 1.16 | — | 0.58 | 0.58 | 0.60 | — | — | — |
| CO | 0.87 | — | 0.45 | 0.42 | 0.43 | — | — | — |
| $CH_4$ | 49.54 | — | 3.21 | 46.33 | 48.64 | — | — | — |
| $CO_2$ | 10.14 | — | — | 10.14 | 11.28 | 0.08 | 0.08 | — |
| $CH_3Cl$ | 10.02 | — | — | 10.02 | 13.28 | 10.02 | 10.02 | — |
| $CH_2Cl_2$ | 1.65 | 0.85 | — | 2.50 | 2.99 | 1.71 | 1.65 | 0.06 |
| $CHCl_3$ | 0.12 | 1.79 | — | 1.91 | 2.46 | 0.47 | 0.12 | 0.35 |
| $CCl_4$ | 0.01 | 1597.36 | 0.33 | 1597.04 | 2045.93 | 201.19 | 4.02 | 197.17 |
| TOTAL | 79.90 | 1600.0 | 8.33 | 1671.57 | 2128.3 | 213.47 | 15.89 | 197.58 |

THE LUMMUS CO. MATERIAL BALANCE LB MOL/HR

| COMPONENT | STREAM | | | | | | | |
|---|---|---|---|---|---|---|---|---|
| | 113 | 114 | 117 | 121 | 122 | 123 | 124 | 199 |
| $N_2$ | — | — | — | 2.69 | 2.64 | 0.06 | 2.63 | — |
| $O_2$ | — | — | — | 0.60 | 0.59 | 0.02 | 0.58 | — |
| CO | — | — | — | 0.43 | 0.42 | 0.01 | 0.42 | — |
| $CH_4$ | — | — | — | 48.64 | 46.70 | 2.31 | 46.33 | — |
| $CO_2$ | — | — | — | 11.20 | 10.44 | 1.14 | 10.06 | — |
| $CH_3Cl$ | — | — | — | 3.26 | — | 3.26 | — | — |
| $CH_2Cl_2$ | 1.00 | 1.06 | 0.21 | 0.28 | 0.02 | 0.49 | — | — |
| $CHCl_3$ | 1.89 | 2.24 | 0.45 | 0.10 | 0.02 | 0.55 | — | — |
| $CCl_4$ | 1794.97 | 1996.70 | 399.34 | 49.77 | 8.14 | 448.89 | 0.22 | 4.56 |
| TOTAL | 1797.86 | 2000.0 | 400.0 | 116.97 | 68.97 | 456.73 | 60.24 | 4.56 |

The present invention is particularly advantageous in that it provides for purging of inerts from the system, while simultaneously providing a stream for carbon dioxide removal, which is essentially free of low boiling chlorinated hydrocarbons. As a result, the overall operation of the carbon dioxide absorption system is improved.

Numerous modifications and variations of the present invention are possible in light of the above teachings and, therefore, within the scope of the appended claims, the invention may be practiced otherwise than as particularly described.

What is claimed is:

1. In a process for producing chlorinated hydrocarbons in a chlorinated hydrocarbon production zone, the improvement comprising:
   recovering a gas stream comprising unreacted hydrocarbon, at least one low boiling chlorinated hydrocarbon, carbon dioxide and inerts;
   introducing said gas stream into a first absorption zone wherein said gas stream is contacted with a chlorinated hydrocarbon absorption oil having a number of carbon atoms corresponding to the unreacted hydrocarbon and a boiling point of at least 140° F to absorb unreacted hydrocarbon, carbon dioxide and the at least one low boiling chlorinated hydrocarbon from the gas stream;
   withdrawing a rich absorption solution from the first absorption zone and introducing the rich absorption solution into a stripping zone to recover a first stream containing lean absorption solution, a second stream containing unreacted hydrocarbon, carbon dioxide and a minor portion of the at least one low boiling chlorinated hydrocarbon and a third stream containing the at least one low boiling chlorinated hydrocarbon;
introducing the second stream into a second absorption zone wherein the second stream is contacted with the chlorinated hydrocarbon absorption oil under conditions such that the at least one low boiling chlorinated hydrocarbon is selectively absorbed; and
   recovering from the second absorption zone unreacted hydrocarbon and carbon dioxide essentially free of the at least one low boiling chlorinated hydrocarbon.

2. The process of claim 1 wherein rich absorption solution is recovered from the second absorption zone and introduced into the stripping zone.

3. The process of claim 2 wherein the chlorinated hydrocarbon absorption oil and the unreacted hydrocarbon has no more than 2 carbon atoms.

4. The process of claim 2 wherein the third stream is recovered as a side stream from said stripping zone.

5. The process of claim 4 wherein the third stream includes a portion of the chlorinated hydrocarbon absorption oil and further comprising introducing the third stream into a further stripping zone to recover chlorinated hydrocarbon absorption oil and recycling recovered chlorinated hydrocarbon absorption oil to at least one of the first and second absorption zones.

6. The process of claim 5 wherein the first stream recovered from the stripping zone, containing chlorinated hydrocarbon absorption oil is recycled to the first and second absorption zones.

7. The process of claim 6 wherein the contacting in the first and second absorption zone is effected countercurrently.

8. The process of claim 6 wherein the unreacted hydrocarbon and carbon dioxide are introduced into a carbon dioxide absorption zone to absorb carbon dioxide therefrom and unreacted hydrocarbon recovered from the carbon dioxide absorption zone is recycled to the chlorinated hydrocarbon production zone.

9. The process of claim 4 wherein the chlorinated hydrocarbons are chloromethanes, said unreacted hydrocarbon is methane and the chlorinated hydrocarbon absorption oil is selected from the group consisting of chloroform, carbon tetrachloride and mixtures thereof.

10. The process of claim 9 wherein the chlorinated hydrocarbon absorption oil is carbon tetrachloride.

11. The process of claim 10 wherein the gas stream introduced into the first absorption zone contains methyl chloride, methylene chloride and chloroform, said methyl chloride, methylene chloride and chloroform being recovered with carbon tetrachloride absorption oil as said third stream withdrawn from the stripping zone as a side stream.

12. The process of claim 11 wherein the first and second absorption zones are operated at a temperature of from 0° F. to 170° F. and a pressure of from 100 to 300 psig.

13. The process of claim 4 wherein the chlorinated hydrocarbons produced are $C_2$ chlorinated hydrocarbons and the unreacted hydrocarbon is selected from the group consisting of ethane, ethylene and mixtures thereof.

* * * * *